United States Patent [19]
Uchiyama et al.

[11] Patent Number: 5,876,705
[45] Date of Patent: Mar. 2, 1999

[54] CONDITIONING SHAMPOO COMPOSITIONS

[75] Inventors: Hirotaka Uchiyama; John Gregory Schroeder; Yoshinari Okuyama, all of Higashinada-ku, Japan

[73] Assignee: The Procter & Gamble Co., Cincinnati, Ohio

[21] Appl. No.: 873,579

[22] Filed: Jun. 12, 1997

Related U.S. Application Data

[63] Continuation of Ser. No. 543,778, Oct. 16, 1995, abandoned.

[51] Int. Cl.$^6$ .............................. A01K 7/00; A01K 7/06
[52] U.S. Cl. ................................ 424/70.12; 424/70.11; 424/70.17
[58] Field of Search ............................ 424/70.11, 70.17, 424/70.12

[56] References Cited

U.S. PATENT DOCUMENTS

| | | | |
|---|---|---|---|
| 2,897,178 | 7/1959 | Hill | 260/45.9 |
| 2,921,047 | 1/1960 | Smith | 260/45.9 |
| 2,934,518 | 4/1960 | Smith | 260/45.85 |
| 2,942,978 | 6/1960 | Segel et al. | 99/48 |
| 2,942,979 | 6/1960 | Segel et al. | 99/48 |
| 2,942,980 | 6/1960 | Segel et al. | 99/48 |
| 2,991,229 | 7/1961 | Ivison | 424/49 |
| 2,999,068 | 9/1961 | Pilcher et al. | 252/137 |
| 3,201,257 | 8/1965 | Hamon et al. | 99/113 |
| 3,201,367 | 8/1965 | Smith | 260/45.9 |
| 3,242,115 | 3/1966 | McGary | 260/29.2 |
| 3,326,849 | 6/1967 | Kelly et al. | 260/45.8 |
| 3,374,275 | 3/1968 | Dickey | 260/611.5 |
| 3,634,315 | 1/1972 | Hattori et al. | 260/45.8 |
| 3,645,950 | 2/1972 | Stratta | 260/29.2 |
| 3,729,441 | 4/1973 | Tomomatsu | 260/45.95 |
| 3,783,872 | 1/1974 | King | 128/290 |
| 3,811,349 | 5/1974 | Jennings | 83/14 |
| 3,944,663 | 3/1976 | Weiss et al. | 424/78 |
| 4,058,474 | 11/1977 | Keyes et al. | 252/160 |
| 4,108,800 | 8/1978 | Froehlich | 252/541 |
| 4,148,743 | 4/1979 | Schubert | 252/132 |
| 4,169,067 | 9/1979 | Joshi | 252/132 |
| 4,192,862 | 3/1980 | Pengilly | 424/47 |
| 4,211,681 | 7/1980 | Braun et al. | 260/29.2 R |
| 4,329,334 | 5/1982 | Su et al. | 424/70.19 |
| 5,358,667 | 10/1994 | Bergman | 252/547 |
| 5,650,384 | 7/1997 | Gordon et al. | 510/159 |

FOREIGN PATENT DOCUMENTS 2822034 12/1987 Japan.

OTHER PUBLICATIONS

Zviak, The Science of Hair Care, pp. 121–125, 1986.
Derwent Accession No. 95–041155/06 (JP06321742–A) English Abstract "Hairdressing material Composition permitting uniform, ready application—contains polyethylene glycol and dimethyl–polysiloxane".
Union Carbide, Specialty Chemicals and Plastics Division, Danbury, CT, Booklet, "Patent Literature Review of Polox Resin Applications".

*Primary Examiner*—Sally Gardner-Lane
*Attorney, Agent, or Firm*—Tara M. Rosnell; Loretta Henderson; David L. Suter

[57] ABSTRACT

The present invention relates to conditioning shampoo compositions which both cleanse the hair and condition the hair. These compositions comprise a detersive surfactant; a fatty compounds; a hair conditioning agent; and water. The present invention also relates to methods for cleansing and conditioning the hair.

30 Claims, No Drawings

CONDITIONING SHAMPOO COMPOSITIONS

This is a continuation of application Ser. No. 08/543,778, filed Oct. 16, 1995 ABN.

FIELD OF THE INVENTION

The present invention relates to conditioning shampoo compositions which both cleanse the hair and condition the hair. These compositions comprise a detersive surfactant; a fatty compounds; a hair conditioning agent; and water. The present invention also relates to methods for cleansing and conditioning the hair.

BACKGROUND OF THE INVENTION

Human hair becomes soiled due to its contact with the surrounding environment and from the sebum secreted by the scalp. The soiling of hair causes it to have a dirty feel and an unattractive appearance. The soiling of the hair necessitates shampooing with frequent regularity.

Shampooing cleans the hair by removing excess soil and sebum. However, shampooing can leave the hair in a wet, tangled, and generally unmanageable state. Once the hair dries, it is often left in a dry, rough, lusterless, or frizzy condition due to removal of the hair's natural oils and other natural conditioning and moisturizing components. The hair can further be left with increased levels of static upon drying, which can interfere with combing and result in a condition commonly referred to as "fly-away hair."

A variety of approaches have been developed to alleviate these after-shampoo problems. These approaches range from post-shampoo application of hair conditioners such as leave-in and rinse-off products, to hair conditioning shampoos which attempt to both cleanse and condition the hair from a single product. Hair conditioners are typically applied in a separate step following shampooing. The hair conditioners are either rinsed-off or left-in, depending upon the type of product used. Hair conditioners, however, have the disadvantage of requiring a separate and inconvenient treatment step. Conditioning shampoos, i.e. shampoos which both cleanse and condition the hair, are highly desirable products because they are convenient for consumers to use.

In order to provide hair conditioning benefits in a cleansing shampoo base, a wide variety of conditioning actives have been proposed. However, many of these actives have the disadvantage of leaving the hair feeling soiled or coated, of interfering with the cleansing efficacy of the shampoo, or of yielding a resultant shampoo with poor shelf stability.

It has surprisingly been found in the present invention that stable shampoo compositions having good cleansing and conditioning ability without leaving the hair feeling soiled or coated can be achieved. These compositions provide improved wet hair conditioning benefits such as smoothness and ease of combing compared to conventional conditioning shampoos. These compositions also provide improved dry hair conditioning benefits such as leaving the hair feeling soft, smooth, and moistened. These dry hair benefits can also result in hair that looks shiny. These compositions are achieved by utilizing the combination of a detersive surfactant; selected fatty compounds; a hair conditioning agent selected from the group consisting of nonvolatile dispersed silicone conditioning agents, hydrocarbon conditioning agents, water soluble cationic polymeric conditioning agents, cationic surfactants, and mixtures thereof. Preferred embodiments include compositions which further comprise a polyalkylene glycol.

It is therefore an object of the present invention to provide conditioning shampoo compositions, i.e. compositions which both cleanse and condition the hair from a single product.

It is another object of the present invention to provide compositions which do not leave the hair feeling coated, heavy, or soiled.

It is another object of the present invention to provide compositions which provide improved wet hair conditioning benefits such as smoothness and ease of combing.

It is an object of the present invention to provide compositions which provide improved dry hair conditioning benefits such as leaving the hair feeling soft and smooth and looking shiny.

It is another object of the present invention to provide methods for cleansing and conditioning the hair utilizing a single composition.

These and other objects will become readily apparent from the detailed description which follows.

SUMMARY OF THE INVENTION

The present invention relates to a hair conditioning shampoo composition comprising:

(a) from about 5% to about 50% by weight of a detersive surfactant selected from the group consisting of anionic surfactants, nonionic surfactants, amphoteric surfactants, zwitterionic surfactants, and mixtures thereof;

(b) from about 0.9% to about 10% by weight of a fatty compound selected from the group consisting of fatty alcohols, fatty acids, fatty alcohol derivatives, fatty acid derivatives, and mixtures thereof;

(c) from about 0.05% to about 20% by weight of a hair conditioning agent selected from the group consisting of nonvolatile dispersed silicone conditioning agents, hydrocarbon conditioning agents, water soluble cationic polymeric conditioning agents, cationic surfactants, and mixtures thereof; and (d) from about 20% to about 94.05% by weight water.

In further embodiments, the present invention relates to a hair conditioning shampoo composition comprising:

(a) from about 5% to about 50% by weight of a detersive surfactant selected from the group consisting of anionic surfactants, nonionic surfactants, amphoteric surfactants, zwitterionic surfactants, and mixtures thereof;

(b) from about 0.01% to about 10% by weight of a fatty compound selected from the group consisting of fatty acids, fatty alcohol derivatives, fatty acid derivatives, and mixtures thereof;

(c) from about 0% to about 9.99% by weight of a fatty alcohol;

(d) from about 0.05% to about 20% by weight of a hair conditioning agent selected from the group consisting of nonvolatile dispersed silicone conditioning agents, hydrocarbon conditioning agents, water soluble cationic polymeric conditioning agents, cationic surfactants, and mixtures thereof; and (e) from about 20% to about 94.94% by weight water.

wherein the sum total concentration of said fatty compound selected from the group consisitng of fatty acids, fatty alcohol derivatives, fatty acid derivatives, and mixtures thereof and said fatty alcohol is from about 0.01% to about 10%.

In further embodiments, the present invention relates to a hair conditioning shampoo composition comprising:

(a) from about 5% to about 50% by weight of a detersive surfactant selected from the group consisting of anionic nonionic surfactants, amphoteric surfactants, surfactants, zwitterionic surfactants, and mixtures thereof;

(b) from about 0.01% to about 10% by weight of a fatty compound selected from the group consisting of fatty alcohols, fatty acids, fatty alcohol derivatives, fatty acid derivatives, and mixtures thereof;

(c) from about 0.05% to about 20% by weight of a hair conditioning agent selected from the group consisting of hydrocarbon conditioning agents, water soluble cationic polymeric conditioning agents, cationic surfactants, and mixtures thereof;

(d) from about 0% to about 19.95% by weight of a nonvolatile dispersed silicone conditioning agent; and (e) from about 20% to about 94.94% by weight water, wherein the sum total concentration of said hair conditioning agent selected from the group consisting of hydrocarbon conditioning agents, water soluble cationic polymeric conditioning agents, cationic surfactants, and mixtures thereof and said nonvolatile dispersed silicone conditioning agent is from about 0.05% to about 20%.

The present invention also relates to methods for cleansing and conditioning the hair utilizing these compositions.

Unless otherwise indicated, all percentages and ratios used herein are by weight of the total composition and all measurements are made at 25° C. or room temperature.

The invention hereof can comprise, consist of, or consist essentially of the essential elements and limitations of the invention described herein, as well any of the additional ingredients, components, or limitations described herein. All documents referred to herein are incorporated by reference herein in their entirety.

DETAILED DESCRIPTION OF THE INVENTION

The compositions of the present invention comprise the following essential as well as optional components.

Detersive Surfactant

The compositions of the present invention comprise a detersive surfactant selected from the group consisting of one or more anionic, nonionic, amphoteric, or zwitterionic surfactants, or mixtures thereof. The purpose of the detersive surfactant is to provide cleansing performance to the composition. The term detersive surfactant, as used herein, is intended to distinguish these surfactants from surfactants which are primarily emulsifying surfactants, i.e. surfactants which provide an emulsifying benefit and which have low cleansing performance. It is recognized that most surfactants have both detersive and emulsifying properties. It is not intended to exclude emulsifying surfactants from the present invention, provided the surfactant also possesses sufficient detersive properties to be useful herein.

The detersive surfactant will generally comprise from about 5% to about 50%, preferably from about 8% to about 30%, and more preferably from about 10% to about 25%, by weight of the composition.

Anionic Surfactants

Anionic surfactants useful herein include alkyl and alkyl ether sulfates. These materials have the respective formulae $ROSO_3M$ and $RO(C_2H_4O)_xSO_3M$, wherein R is alkyl or alkenyl of from about 8 to about 30 carbon atoms, x is 1 to about 10, and M is hydrogen or a cation such as anmmonium, alkanolammonium (e.g., triethanolammonium), a monovalent metal cation (e.g., sodium and potassium), or a polyvalent metal cation (e.g., magnesium and calcium). Preferably, M should be chosen such that the anionic surfactant component is water soluble. The anionic surfactant or surfactants should be chosen such that the Krafft temperature is about 15° C. or less, preferably about 10° C. or less, and more preferably about 0° or less. It is also preferred that the anionic surfactant be soluble in the composition hereof.

Krafft temperature refers to the point at which solubility of an ionic surfactant becomes determined by crystal lattice energy and heat of hydration, and corresponds to a point at which solubility undergoes a sharp, discontinuous increase with increasing temperature. Each type of surfactant will have its own characteristic Krafft temperature. Krafft temperature for ionic surfactants is, in general, well known and understood in the art. See, for example, Myers, Drew, *Surfactant Science and Technology*, pp. 82–85, VCH Publishers, Inc. (New York, N.Y., USA), 1988 (ISBN 0-89573-399-0), which is incorporated by reference herein in its entirety.

In the alkyl and alkyl ether sulfates described above, preferably R has from about 12 to about 18 carbon atoms in both the alkyl and alkyl ether sulfates. The alkyl ether sulfates are typically made as condensation products of ethylene oxide and monohydric alcohols having from about 8 to about 24 carbon atoms. The alcohols can be derived from fats, e.g., coconut oil, palm oil, tallow, or the like, or the alcohols can be synthetic. Lauryl alcohol and straight chain alcohols derived from coconut oil and palm oil are preferred herein. Such alcohols are reacted with 1 to about 10, and especially about 3, molar proportions of ethylene oxide and the resulting mixture of molecular species having, for example, an average of 3 moles of ethylene oxide per mole of alcohol, is sulfated and neutralized.

Specific examples of alkyl ether sulfates which can be used in the present invention are sodium and ammonium salts of coconut alkyl triethylene glycol ether sulfate; tallow alkyl triethylene glycol ether sulfate, and tallow alkyl hexaoxyethylene sulfate. Highly preferred alkyl ether sulfates are those comprising a mixture of individual compounds, said mixture having an average alkyl chain length of from about 12 to about 16 carbon atoms and an average degree of ethoxylation of from 1 to about 4 moles of ethylene oxide. Such a mixture also comprises from 0% to about 20% by weight $C_{12-13}$ compounds; from about 60% to about 100% by weight of $C_{14-15-16}$ compounds, from 0% to about 20% by weight of $C_{17-18-19}$ compounds; from about 3% to about 30% by weight of compounds having a degree of ethoxylation of 0; from about 45% to about 90% by weight of compounds having a degree of ethoxylation of from 1 to about 4; from about 10% to about 25% by weight of compounds having a degree of ethoxylation of from about 4 to about 8; and from about 0.1% to about 15% by weight of compounds having a degree of ethoxylation greater than about 8.

Other suitable anionic surfactants are the water-soluble salts of organic, sulfuric acid reaction products of the general formula $[R_1—SO_3—M]$ where $R_1$ is selected from the group consisting of a straight or branched chain, saturated aliphatic hydrocarbon radical having from about 8 to about 24, preferably about 10 to about 18, carbon atoms; and M is as previously described above in this section. Examples of such surfactants are the salts of an organic sulfuric acid reaction product of a hydrocarbon of the methane series, including iso-, neo-, and n-paraffins, having about 8 to about 24 carbon atoms, preferably about 12 to about 18 carbon atoms and a sulfonating agent, e.g., $SO_3$, $H_2SO_4$, obtained according to known sulfonation methods, including bleaching and hydrolysis. Preferred are alkali metal and ammonium sulfonated $C_{10-18}$ n-paraffins.

Still other suitable anionic surfactants are the reaction products of fatty acids esterified with isethionic acid and neutralized with sodium hydroxide where, for example, the fatty acids are derived from coconut or palm oil; or sodium or potassium salts of fatty acid amides of methyl tauride in which the fatty acids, for example, are derived from coconut oil. Other similar anionic surfactants are described in U.S. Pat. Nos. 2,486,921, 2,486,922, and 2,396,278, which are incorporated by reference herein in their entireties.

Other anionic surfactants suitable for use in the shampoo compositions are the succinates, examples of which include disodium N-octadecylsulfosuccinate; disodium lauryl sulfosuccinate; diammonium lauryl sulfosuccinate; tetra sodium N-(1,2-dicarboxyethyl)-N-octadecylsulfosuccinate; the diamyl ester of sodium sulfosuccinic acid; the dihexyl ester of sodium sulfosuccinic acid; and the dioctyl ester of sodium sulfosuccinic acid.

Other anionic surfactants suitable for use in the shampoo compositions are those that are derived from amino acids. Nonlimiting examples of such surfactants include N-acyl-L-glutamate, N-acyl-N-methyl-β-alanate, N-acylsarcosinate, and their salts.

Still other useful surfactants are those that are derived from taurine, which is also known as 2-aminoethanesulfonic acid. An example of such an acid is N-acyl-N-methyl taurate.

Other suitable anionic surfactants include olefin sulfonates having about 10 to about 24 carbon atoms. The term "olefin sulfonates" is used herein to mean compounds which can be produced by the sulfonation of alpha-olefins by means of uncomplexed sulfur trioxide, followed by neutralization of the acid reaction mixture in conditions such that any sulfones which have been formed in the reaction are hydrolyzed to give the corresponding hydroxy-alkanesulfonates. The sulfur trioxide can be liquid or gaseous, and is usually, but not necessarily, diluted by inert diluents, for example by liquid $SO_2$, chlorinated hydrocarbons, etc., when used in the liquid form, or by air, nitrogen, gaseous $SO_2$, etc., when used in the gaseous form.

The alpha-olefins from which the olefin sulfonates are derived are mono-olefins having about 12 to about 24 carbon atoms, preferably about 14 to about 16 carbon atoms. Preferably, they are straight chain olefins.

In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process. A specific alpha-olefin sulfonate mixture of the above type is described more fully in U.S. Pat. No. 3,332,880, to Pflaumer and Kessler, issued Jul. 25, 1967, which is incorporated by reference herein in its entirety.

Another class of anionic surfactants suitable for use in the shampoo compositions are the beta-alkyloxy alkane sulfonates. These compounds have the following formula:

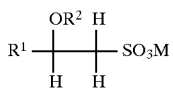

where $R^1$ is a straight chain alkyl group having from about 6 to about 20 carbon atoms, $R^2$ is a lower alkyl group having from about 1, preferred, to about 3 carbon atoms, and M is as hereinbefore described. Many other anionic surfactants suitable for use in the shampoo compositions are described in *McCutcheon's, Emulsifiers and Detergents*, 1989 *Annual*, published by M. C. Publishing Co., and in U.S. Pat. No. 3,929,678, which descriptions are incorporated herein by reference in their entirety. Preferred anionic surfactants for use in the shampoo compositions include amunonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, and sodium dodecyl benzene sulfonate, sodium N-lauroyl-L-glutamate, triethanol N-lauryoyl-L-glutamate, sodium N-lauroyl-N-methyl taurate, sodium N-lauroyl-N-methyl-β-aminopropionate, and mixtures thereof.

Amphoteric and Zwitterionic Surfactants

The shampoo compositions can comprise amphoteric and/or zwitterionic surfactants.

Amphoteric surfactants for use in the shampoo compositions include the derivatives of aliphatic secondary and tertiary amines in which the aliphatic radical is straight or branched and one of the aliphatic substituents contains from about 8 to about 18 carbon atoms and one contains an anionic water solubilizing group, e.g., carboxy, sulfonate, sulfate, phosphate, or phosphonate.

Zwitterionic surfactants for use in the shampoo compositions include the derivatives of aliphatic quaternary ammonium, phosphonium, and sulfonium compounds, in which the aliphatic radicals are straight or branched, and wherein one of the aliphatic substituents contains from about 8 to about 18 carbon atoms and one contains an anionic group, e.g., carboxy, sulfonate, sulfate, phosphate, or phosphonate. A general formula for these compounds is:

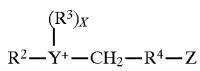

where $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing 1 to about 3 carbon atoms; X is 1 when Y is a sulfur atom, and 2 when Y is a nitrogen or phosphorus atom; $R^4$ is an alkylene or hydroxyalkylene of from 1 to about 4 carbon atoms and Z is a radical selected from the group consisting of carboxylate, sulfonate, sulfate, phosphonate, and phosphate groups.

Examples of amphoteric and zwitterionic surfactants also include sultaines and amidosultaines. Sultaines, including amidosultaines, include for example, cocodimethylpropylsultaine, stearyldimethylpropylsultaine, lauryl-bis-(2-hydroxyethyl) propylsultaine and the like; and the amidosultaines such as cocamidodimethylpropylsultaine, stearylamidododimethylpropylsultaine, laurylamidobis-(2-hydroxyethyl) propylsultaine, and the like. Preferred are amidohydroxysultaines such as the $C_{12}$–$C_{18}$ hydrocarbyl amidopropyl hydroxysultaines, especially $C_{12}$–$C_{14}$ hydrocarbyl amido propyl hydroxysultaines, e.g., laurylamidopropyl hydroxysultaine and cocamidopropyl hydroxysultaine. Other sultaines are described in U.S. Pat. No. 3,950,417, which is incorporated herein by reference in its entirety.

Other suitable amphoteric surfactants are the aminoalkanoates of the formula R—NH(CH$_2$)$_n$COOM, the iminodialkanoates of the formula R—N[(CH$_2$)$_m$COOM]$_2$ and mixtures thereof; wherein n and m are numbers from 1 to about 4, R is $C_8$–$C_{22}$ alkyl or alkenyl, and M is hydrogen, alkali metal, alkaline earth metal, ammonium or alkanolammonium.

Examples of suitable aminoalkanoates include n-alkylamino-propionates and n-alkyliminodipropionates, specific examples of which include N-lauryl-beta-amino propionic acid or salts thereof, and N-lauryl-beta-iminodipropionic acid or salts thereof, and mixtures thereof.

Other suitable amphoteric surfactants include those represented by the formula:

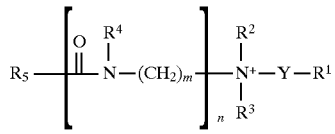

wherein $R^1$ is $C_8$–$C_{22}$ alkyl or alkenyl, preferably $C_{12}$–$C_{16}$, $R^2$ and $R^3$ is independently selected from the group consisting of hydrogen, CH$_2$CO$_2$M, CH$_2$CH$_2$OH, CH$_2$CH$_2$OCH$_2$CH$_2$COOM, or (CH$_2$CH$_2$O)$_m$H wherein m is an integer from 1 to about 25, and $R^4$ is hydrogen, CH$_2$CH$_2$OH, or CH$_2$CH$_2$OCH$_2$CH$_2$COOM, Z is CO$_2$M or CH$_2$CO$_2$M, n is 2 or 3, preferably 2, M is hydrogen or a cation, such as alkali metal (e.g., lithium, sodium, potassium), alkaline earth metal (beryllium, magnesium, clacium, strontium, barium), or ammonium. This type of surfactant is sometimes classified as an imidazoline-type amphoteric surfactant, although it should be recognized that it does not necessarily have to be derived, directly or indirectly, through an imidazoline intermediate. Suitable materials of this type are marketed under the tradename MIRANOL and are understood to comprise a complex mixture of species, and can exist in protonated and non-protonated species depending upon pH with respect to species that can have a hydrogen at $R^2$. All such variations and species are meant to be encompassed by the above formula.

Examples of surfactants of the above formula are monocarboxylates and dicarboxylates. Examples of these materials include cocoamphocarboxypropionate, cocoamphocarboxypropionic acid, cocoamphocarboxyglycinate (alternately referred to as cocoamphodiacetate), and cocoamphoacetate.

Commercial amphoteric surfactants include those sold under the trade names MIRANOL C2M CONC. N.P., MIRANOL C2M CONC. O.P., MIRANOL C2M SF, MIRANOL CM SPECIAL (Miranol, Inc.); ALKATERIC 2CIB (Alkaril Chemicals); AMPHOTERGE W-2 (Lonza, Inc.); MONATERIC CDX-38, MONATERIC CSH-32 (Mona Industries); REWOTERIC AM-2C (Rewo Chemical Group); and SCHERCOTERIC MS-2 (Scher Chemicals).

Betaine surfactants, i.e. zwitterionic surfactants, suitable for use in the shampoo compositions are those represented by the formula:

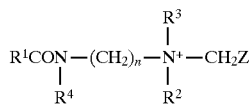

wherein:

$R_1$ is a member selected from the group consisting of

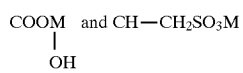

$R_2$ is lower alkyl or hydroxyalkyl;

$R_3$ is lower alkyl or hydroxyalkyl;

$R_4$ is a member selected from the group consisting of hydrogen and lower alkyl;

$R_5$ is higher alkyl or alkenyl;

Y is lower alkyl, preferably methyl;

m is an integer from 2 to 7, preferably from 2 to 3;

n is the integer 1 or 0;

M is hydrogen or a cation, as previously described, such as an alkali metal, alkaline earth metal, or ammonium. The term "lower alkyl" or "hydroxyalkyl" means straight or branch chained, saturated, aliphatic hydrocarbon radicals and substituted hydrocarbon radicals having from one to about three carbon atoms such as, for example, methyl, ethyl, propyl, isopropyl, hydroxypropyl, hydroxyethyl, and the like. The term "higher alkyl or alkenyl" means straight or branch chained saturated (i.e., "higher alkyl") and unsaturated (i.e., "higher alkenyl") aliphatic hydrocarbon radicals having from about eight to about 20 carbon atoms such as, for example, lauryl, cetyl, stearyl, oleyl, and the like. It should be understood that the term "higher alkyl or alkenyl" includes mixtures of radicals which may contain one or more intermediate linkages such as ether or polyether linkages or non-functional substitutents such as hydroxyl or halogen radicals wherein the radical remains of hydrophobic character.

Examples of surfactant betaines of the above formula wherein n is zero which are useful herein include the alkylbetaines such as cocodimethylcarboxymethylbetaine, lauryldimethylcarboxymethylbetaine, lauryl dimethyl-alpha-carboxyethylbetaine, cetyldimethylcarboxymethylbetaine, lauryl-bis-(2-hydroxyethyl)carboxymethylbetaine, stearyl-bis-(2-hydroxypropyl)carboxymethylbetaine, oleyldimethyl-gamma-carboxypropylbetaine, lauryl-bix-(2-hydroxypropyl)alpha-carboxyethylbetaine, etc. The sulfobetaines may be represented by cocodimethylsulfopropylbetaine, stearyldimethylsulfopropylbetaine, lauryl-bis-(2-hydroxyethyl)sulfopropylbetaine, and the like.

Specific examples of amido betaines and amidosulfo betaines useful in the shampoo compositions include the amidocarboxybetaines, such as cocamidodimethylcarboxymethylbetaine, laurylamidodimethylcarboxymethylbetaine, cetylamidodimethylcarboxymethylbetaine, laurylamido-bis-(2-hydroxyethyl)-carboxymethylbetaine, cocamido-bis-(2-hydroxyethyl)-carboxymethylbetaine, etc. The amido sulfobetaines may be represented by cocamidodimethylsulfopropylbetaine, stearylamidodimethylsulfopropylbetaine, laurylamido-bis-(2-hydroxyethyl)-sulfopropylbetaine, and the like.

Nonionic Surfactants

The shampoo compostions of the present invention can comprise a nonionic surfactant. Nonionic surfactants include those compounds produced by condensation of alkylene oxide groups, hydrophilic in nature, with an organic hydrophobic compound, which may be aliphatic or alkyl aromatic in nature.

Preferred nonlimiting examples of nonionic surfactants for use in the shampoo compositions include the following:

(1) polyethylene oxide condensates of alkyl phenols, e.g., the condensation products of alkyl phenols having an alkyl group containing from about 6 to about 20 carbon atoms in either a straight chain or branched chain configuration, with ethylene oxide, the said ethylene oxide being present in amounts equal to from about 10 to about 60 moles of ethylene oxide per mole of alkyl phenol;

(2) those derived from the condensation of ethylene oxide with the product resulting from the reaction of propylene oxide and ethylene diamine products;

(3) condensation products of aliphatic alcohols having from about 8 to about 18 carbon atoms, in either straight chain or branched chain configurations, with ethylene oxide, e.g., a coconut alcohol ethylene oxide condensate having from about 10 to about 30 moles of ethylene oxide per mole of coconut alcohol, the coconut alcohol fraction having from about 10 to about 14 carbon atoms;

(4) long chain tertiary amine oxides of the formula $[R^1R^2R^3N\rightarrow O]$ where $R^1$ contains an alkyl, alkenyl or monohydroxy alkyl radical of from about 8 to about 18 carbon atoms, from 0 to about 10 ethylene oxide moieties, and from 0 to about 1 glyceryl moiety, and $R^2$ and $R^3$ contain from about 1 to about 3 carbon atoms and from 0 to about 1 hydroxy group, e.g., methyl, ethyl, propyl, hydroxyethyl, or hydroxypropyl radicals;

(5) long chain tertiary phosphine oxides of the formula $[RR'R''P\rightarrow O]$ where R contains an alkyl, alkenyl or monohydroxyalkyl radical ranging from about 8 to about 18 carbon atoms in chain length, from 0 to about 10 ethylene oxide moieties and from 0 to 1 glyceryl moieties and R' and R" are each alkyl or monohydroxyalkyl groups containing from about 1 to about 3 carbon atoms;

(6) long chain dialkyl sulfoxides containing one short chain alkyl or hydroxy alkyl radical of from 1 to about 3 carbon atoms (usually methyl) and one long hydrophobic chain which include alkyl, alkenyl, hydroxy alky, or keto alkyl radicals containing from about 8 to about 20 carbon atoms, from 0 to about 10 ethylene oxide moieties and from 0 to 1 glyceryl moieties;

(7) alkyl polysaccharide (APS) surfactants (e.g. alkyl polyglycosides), examples of which are described in U.S. Pat. No. 4,565,647, which is incorporated herein by reference in its entirety, and which discloses APS surfactants having a hydrophobic group with about 6 to about 30 carbon atoms and a polysaccharide (e.g., polyglycoside) as the hydrophilic group; optionally, there can be a polyalkylene-oxide group joining the hydrophobic and hydrophilic moieties; and the alkyl group (i.e., the hydrophobic moiety) can be saturated or unsaturated, branched or unbranched, and unsubstituted or substituted (e.g., with hydroxy or cyclic rings); a preferred material is alkyl polyglucoside which is commercially available from Henkel, ICI Americas, and Seppic; and (8) polyoxyethylene alkyl ethers such as those of the formula $RO(CH_2CH_2)_nH$ and polyethylene glycol (PEG) glyceryl fatty esters, such as those of the formula $R(O)OCH_2CH(OH)CH_2(OCH_2CH_2)_nOH$, wherein n is from 1 to about 200, preferably from about 20 to about 100, and R is an alkyl having from about 8 to about 22 carbon atoms.

Fatty Compounds: Fatty Alcohols, Fatty Acids, Fatty Alcohol Derivatives, And Fatty Acid Derivatives In one set of embodiments, the compositions of the present invention comprise from about 0.9% to about 10%, preferably from about 1.0% to about 10%, more preferably from about 1.1% to about 8%, and even more preferably from about 1.2% to about 5% of one or more fatty compounds selected from the group consisting of fatty alcohols, fatty acids, fatty alcohol derivatives, fatty acid derivatives, and mixtures thereof.

In a further set of embodiments, the compositions of the present invention comprise from about 0.01% to about 10%, preferably from about 0.6% to about 8%, more preferably from about 0.9% to about 5%, and even more preferably from about 1% to about 5% of one or more fatty compounds selected from the group consisting of fatty acids, fatty alcohol derivaives, fatty acid derivatives, and mixtures thereof; in combination with from 0% to 9.99%, preferably from 0% to about 7.4%, more preferably from 0% to about 4.1%, and even more preferably from 0% to about 4% of a fatty alcohol. In these embodiments, the sum total weight percentage of the fatty compound selected from the group consisting of fatty acids, fatty alcohol derivaives, fatty acid derivatives, and mixtures thereof, and the fatty alcohol comprises from about 0.01% to about 10%; preferably from about 0.6% to about 8%, more preferably from about 0.9% to about 5%, and even more preferably from about 1% to about 5% of the total composition.

The term fatty compounds is defined herein to include compounds selected from the group consisting of fatty alcohols, fatty acids, fatty alcohol derivatives, fatty acid derivatives, and also mixtures of one or more hereof. As defined in the prevsious paragraph, it is recognized that the fatty alcohol component of the fatty compound can comprise 0%, by weight of the total composition. It is recongized that the compounds disclosed in this section of the specification can in some instances fall into more than one classification, e.g., some fatty alcohol derivatives can also be classified as fatty acid derivatives. Also, it is recognized that some of these compounds can have properties as nonionic surfactants and can alternatively be classified as such. However, a given classification is not intendend to be a limitation on that particular compound, but is done so for convenience of classification and nomenclature. Nonlimiting examples of the fatty alcohols, fatty acids, fatty alcohol derivatives, and fatty acid derivatives are found in *International Cosmetic Ingredient Dictionary*, Fifth Edition, 1993, and *CTFA Cosmetic Ingredient Handbook*, Second Edition, 1992, both of which are incorporated by reference herein in their entirety.

Fatty Alcohols

The fatty alcohols useful herein are those having from about 10 to about 30 carbon atoms, preferably from about 12 to about 22 carbon atoms, and more preferably from about 16 to about 22 carbon atoms. These fatty alcohols can be straight or branched chain alcohols and can be saturated or unsaturated. Nonlimiting examples of fatty alcohols include decyl alcohol, undecyl alcohol, dodecyl, myristyl, cetyl alcohol, stearyl alcohol, isostearyl alcohol, isocetyl alcohol, behenyl alcohol, linalool, oleyl alcohol, cholesterol, cis-4-t-butylcyclohexanol, myricy alcohol and mixtures thereof. Especially preferred fatty alcohols are those selected from the group consisting of cetyl alcohol, stearyl alcohol, isostearyl alcohol, oleyl alcohol, and mixtures thereof.

Fatty Acids

The fatty acids useful herein are those having from about 10 to about 30 carbon atoms, preferably from about 12 to about 22 carbon atoms, and more preferably from about 16 to about 22 carbon atoms. These fatty acids can be straight or branched chain acids and can be saturated or unsaturated. Also included are diacids, triacids, and other multiple acids which meet the carbon number requirement herein. Also included herein are salts of these fatty acids. Nonlimiting examples of fatty acids include lauric acid, palmitic acid, stearic acid, behenic acid, arichidonic acid, oleic acid, isostearic acid, sebacic acid, and mixtures thereof. Especially preferred for use herein are the fatty acids selected from the group consisting of palmitic acid, stearic acid, and mixtures thereof.

Fatty Alcohol Derivatives

The fatty alcohol derivatives are defined herein to include alkyl ethers of fatty alcohols, alkoxylated fatty alcohols, alkyl ethers of alkoxylated fatty alcohols, esters of fatty alcohols and mixtures thereof. Nonlimiting examples of fatty alcohol derivatives include materials such as methyl stearyl ether; 2-ethylhexyl dodecyl ether; stearyl acetate; cetyl propionate; the ceteth series of compounds such as ceteth-1 through ceteth-45, which are ethylene glycol ethers of cetyl alcochol, wherein the numeric designation indicates the number of ethylene glycol moieties present; the steareth series of compounds such as steareth-1 through 100, which are ethylene glycol ethers of steareth alcohol, wherein the numeric designation indicates the number of ethylene glycol moieties present; ceteareth 1 through ceteareth-50, which are the ethylene glycol ethers of ceteareth alcohol, i.e. a mixture of fatty alcohols containing predominantly cetyl and stearyl alcohol, wherein the numeric designation indicates the number of ethylene glycol moieties present; C1–C30 alkyl ethers of the ceteth, steareth, and ceteareth compounds just described; polyoxyethylene ethers of branched alcohols such as octyldodecyl alochol, dodecylpentadecyl alcohol, hexyldecyl alcohol, and isostearyl alcohol; polyoxyethylene ethers of behenyl alcohol; PPG ethers such as PPG-9-steareth-3, PPG-11 stearyl ether, PPG-8-ceteth-1, and PPG-10 cetyl ether; and mixtures of all of the foregoing compounds. Preferred for use herein are steareth-2, steareth-4, ceteth-2, and mixtures thereof.

Fatty Acid Derivatives

The fatty acid derivatives are defined herein to include fatty acid esters of the fatty alcohols as defined above in this section, fatty acid esters of the fatty alcohol derivatives as defined above in this section when such fatty alcohol derivatives have an esterifiable hydroxyl group, fatty acid esters of alcohols other than the fatty alcohols and the fatty alcohol derivatives described above in this section, hydroxy-substitued fatty acids, and mixtures thereof. Nonlimiting examples of fatty acid derivatives include ricinoleic acid, glycerol monostearate, 12-hydroxy stearic acid, ethyl stearate, cetyl stearate, cetyl palmitate, polyoxyethylene cetyl ether stearate, polyoxyethylene stearyl ether stearate, polyoxyethylene lauryl ether stearate, ehtyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, dimethyl sebacate, PEG-15 cocoate, PPG-15 stearate, glyceryl monostearate, glyceryl distearate, glyceryl tristearate, PEG-8 laurate, PPG-2 isostearate, PPG-9 laurate, and mixtures thereof. Preferred for use herein are glycerol monostearate, 12-hydroxy stearic acid, and mixtures thereof.

Hair Conditioning Agent

The compositions of the present invention comprise from about 0.05% to about 20%, preferably from about 0.1% to about 10%, and more preferably from about 0.5% to about 10% of a hair conditioning agent selected from the group consisting of nonvolatile dispersed silicone conditioning agents, hydrocarbon conditioning agents, water soluble cationic polymeric conditioning agents, cationic surfactants, and mixtures thereof.

In a further set of embodiments, the compositions of the present invention comprise from about 0.05% to about 20%, preferably from about 0.1% to about 10%, and more preferably from about 0.5% to about 10% of a hair conditioning agent selected from the group consisting of hydrocarbon conditioning agents, water soluble cationic polymeric conditioning agents, cationic surfactants, and mixtures thereof, in combination with 0% to about 19.95%, preferably from 0% to about 9.9%, and more preferably from 0% to about 9.5% of a nonvolatile dispersed silicone conditioning agent. In these embodiments the sum total weight percentage of the hair conditioning agent selected from the group consisting of hydrocarbon conditioning agents, water soluble cationic polymeric conditioning agents, cationic surfactants, and mixtures thereof, and the nonvolatile dispersed silicone conditioning agent is from about 0.05% to about 20%, preferably from about 0.1% to about 10%, and more preferably from about 0.5% to about 10% of the total composition.

As defined in the prevsious paragraph, it is recognized that the dispersed silicone conditioning agent can comprise 0%, by weight of the total composition.

Nonvolatile Dispersed Silicone Conditioning Agents

Hair conditioning agents useful herein include nonvolatile, dispersed silicone conditioning agents. By nonvolatile is meant that the silicone conditioning agent exhibits very low or no significant vapor pressure at ambient conditions, e.g., 1 atmosphere at 25° C. The nonvolatile dispersed silicone conditioning agent preferably has a boiling point at ambient pressure of about 250° C. or higher, preferably of about 260° C., and more preferably of about 275° C. By dispersed is meant that the conditioning agent forms a separate, discontinuous phase from the aqueous carrier such as in the form of an emulsion or a suspension of droplets. The droplets have an average particle diameter from about 0.1 microns to about 25 microns, preferably from about 5 microns to about 20 microns.

The nonvolatile silicone hair conditioning agent for use herein will preferably have a viscosity of from about 1,000 to about 2,000,000 centistokes at 25° C., more preferably from about 10,000 to about 1,800,000, and even more preferably from about 100,000 to about 1,500,000. The viscosity can be measured by means of a glass capillary viscometer as set forth in Dow Corning Corporate Test Method CTM0004, Jul. 20, 1970, which is incorporated by reference herein in its entirety. Suitable silicone fluids include polyalkyl siloxanes, polyaryl siloxanes, polyalkylaryl siloxanes, polyether siloxane copolymers, and mixtures thereof. Other nonvolatile silicones having hair conditioning properties can also be used.

The silicones herein also include polyalkyl or polyaryl siloxanes with the following structure:

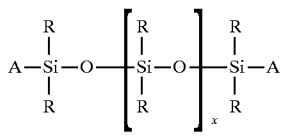

wherein R is alkyl or aryl, and x is an integer from about 7 to about 8,000. "A" represents groups which block the ends of the silicone chains. The alkyl or aryl groups substituted on the siloxane chain (R) or at the ends of the siloxane chains (A) can have any structure as long as the resulting silicone remains fluid at room temperature, is dispersible, is neither irritating, toxic nor otherwise harmful when applied to the hair, is compatible with the other components of the composition, is chemically stable under normal use and storage conditions, and is capable of being deposited on and conditions the hair. Suitable A groups include hydroxy, methyl, methoxy, ethoxy, propoxy, and aryloxy. The two R groups on the silicon atom may represent the same group or different groups. Preferably, the two R groups represent the same group. Suitable R groups include methyl, ethyl, propyl, phenyl, methylphenyl and phenylmethyl. The preferred silicones are polydimethyl siloxane, polydiethylsiloxane, and polymethylphenylsiloxane. Polydimethylsiloxane, which is also known as dimethicone, is especially preferred. The polyalkylsiloxanes that can be used include, for example, polydimethylsiloxanes. These silocones are available, for example, from the General Electric Company in their Viscasil® and SF 96 series, and from Dow Corning in their Dow Corning 200 series.

Polyalkylaryl siloxane fluids can also be used and include, for example, polymethylphenylsiloxanes. These siloxanes are available, for example, from the General Electric Company as SF 1075 methyl phenyl fluid or from Dow Corning as 556 Cosmetic Grade Fluid.

Especially preferred, for enhancing the shine characteristics of hair, are highly arylated silicones, such as highly phenylated polyethyl silicone having refractive indices of about 1.46 or higher, especially about 1.52 or higher. When these high refractive index silicones are used, they should be mixed with a spreading agent, such as a surfactant or a silicone resin, as described below to decrease the surface tension and enhance the film forming ability of the material.

The silicones that can be used include, for example, a polypropylene oxide modified polydimethylsiloxane although ethylene oxide or mixtures of ethylene oxide and propylene oxide can also be used. The ethylene oxide and polypropylene oxide level should be sufficiently low so as not to interfere with the dispersibility characteristics of the silicone. These material are also known as dimethicone copolyols.

Other silicones include amino substituted materials. Suitable alkylamino substituted silicones include those represented by the following structure (II)

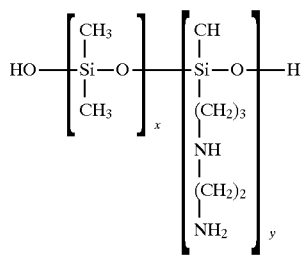

wherein x and y are integers which depend on the molecular weight, the average molecular weight being approximately between 5,000 and 10,000. This polymer is also known as "amodimethicone".

Suitable cationic silicone fluids include those represented by the formula (III) $(R_1)_a G_{3-a}$—Si—$(-OSiG_2)_n$-$(-OSiG_b(R_1)_{2-b})_m$—O—$SiG_{3-a}(R_1)_a$ in which G is chosen from the group consisting of hydrogen, phenyl, OH, $C_1$–$C_8$ alkyl and preferably methyl; a denotes 0 or an integer from 1 to 3, and preferably equals 0; b denotes 0 or 1 and preferably equals 1; the sum n+m is a number from 1 to 2,000 and preferably from 50 to 150, n being able to denote a number from 0 to 1,999 and preferably from 49 to 149 and m being able to denote an integer from 1 to 2,000 and preferably from 1 to 10; $R_1$ is a monovalent radical of formula $CqH_{2q}L$ in which q is an integer from 2 to 8 and L is chosen from the groups —$N(R_2)CH_2$—$CH_2$—$N(R_2)_2$
—$N(R_2)_2$
—$N(R_2)_3 A^-$
—$N(R_2)CH_2$—$CH_2$—$NR_2H_2A^-$ in which $R_2$ is chosen from the group consisting of hydrogen, phenyl, benzyl, a saturated hydrocarbon radical, preferably an alkyl radical containing from 1 to 20 carbon atoms, and $A^-$ denotes a halide ion.

An especially preferred cationic silicone corresponding to formula (III) is the polymer known as "trimethylsilylamodimethicone", of formula (IV):

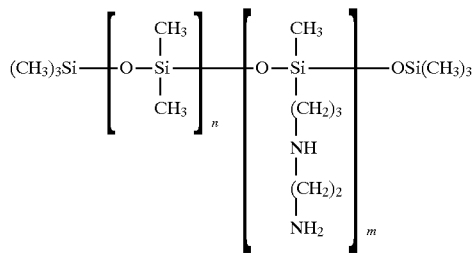

In this formula n and m are selected depending on the exact molecular weight of the compound desired.

Other silicone cationic polymers which can be used in the shampoo compositions are represented by the formula (V):

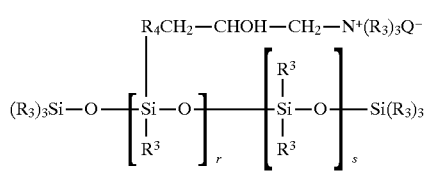

where $R^3$ denotes a monovalent hydrocarbon radical having from 1 to 18 carbon atoms, preferably an alkyl or alkenyl radical such as methyl; $R_4$ denotes a hydrocarbon radical, preferably a $C_1$–$C_{18}$ alkylene radical or a $C_1$–$C_{18}$, and more preferably $C_1$–$C_8$, alkyleneoxy radical; $Q^-$ is a halide ion, preferably chloride; r denotes an average statistical value from 2 to 20, preferably from 2 to 8; s denotes an average statistical value from 20 to 200, and preferably from 20 to 50. A preferred polymer of this class is available from Union Carbide under the name "UCAR SILICONE ALE 56."

References disclosing suitable silicones include U.S. Pat. No. 2,826,551, to Geen; U.S. Pat. No. 3,964,500, to Drakoff, issued Jun. 22, 1976; U.S. Pat. No. 4,364,837, to Pader; and British Patent No. 849,433, to Woolston, all of which are incorporated herein by reference in their entirety. Also incorporated herein by reference in its entirety is "Silicon Compounds" distributed by Petrarch Systems, Inc., 1984. This reference provides an extensive, though not exclusive, listing of suitable silicones.

Another silicone hair conditioning material that can be especially useful is a silicone gum. The term "silicone gum", as used herein, means a polyorganosiloxane material having a viscosity at 25° C. of greater than or equal to 1,000,000 centistokes. It is recognized that the silicone gums described herein can also have some overlap with the above-disclosed silicones. This overlap is not intended as a limitation on any of these materials. Silicone gums are described by Petrarch, Id., and others including U.S. Pat. No. 4,152,416, to Spitzer et al., issued May 1, 1979 and Noll, Walter, *Chemistry and Technology of Silicones*, New York: Academic Press 1968. Also describing silicone gums are General Electric Silicone Rubber Product Data Sheets SE 30, SE 33, SE 54 and SE 76. All of these described references are incorporated herein by reference in their entirety. The "silicone gums" will typically have a mass molecular weight in excess of about 200,000, generally between about 200,000 and about 1,000,000. Specific examples include polydimethylsiloxane, (polydimethylsiloxane) (methylvinylsiloxane) copolymer, poly(dimethylsiloxane) (diphenyl siloxane) (methylvinylsiloxane) copolymer and mixtures thereof.

Also useful are silicone resins, which are highly crosslinked polymeric siloxane systems. The crosslinking is introduced through the incorporation of trifunctional and tetrafunctional silanes with monofunctional or difunctional, or both, silanes during manufacture of the silicone resin. As is well understood in the art, the degree of crosslinking that is required in order to result in a silicone resin will vary according to the specific silane units incorporated into the silicone resin. In general, silicone materials which have a sufficient level of trifunctional and tetrafunctional siloxane monomer units, and hence, a sufficient level of crosslinking, such that they dry down to a rigid, or hard, film are considered to be silicone resins. The ratio of oxygen atoms to silicon atoms is indicative of the level of crosslinking in a particular silicone material. Silicone materials which have at least about 1.1 oxygen atoms per silicon atom will generally be silicone resins herein. Preferably, the ratio of oxygen:silicon atoms is at least about 1.2:1.0. Silanes used in the manufacture of silicone resins include monomethyl-, dimethyl-, trimethyl-, monophenyl-, diphenyl-, methylphenyl-, monovinyl-, and methylvinyl-chlorosilanes, and tetrachlorosilane, with the methyl-substituted silanes being most commonly utilized. Preferred resins are offered by General Electric as GE SS4230 and SS4267. Commercially available silicone resins will generally be supplied in a dissolved form in a low viscosity volatile or nonvolatile silicone fluid. The silicone resins for use herein should be supplied and incorporated into the present compositions in such dissolved form, as will be readily apparent to those skilled in the art. Without being limited by theory, it is believed that the silicone resins can enhance deposition of other silicones on the hair and can enhance the glossiness of hair with high refractive index volumes.

Other useful silicone resisns are silicone resin powders such as the material given the CTFA designation polymethylsilsequioxane, which is commercially available as Tospearl™ from Toshiba Silicones.

Background material on silicones, including sections discussing silicone fluids, gums, and resins, as well as the manufacture of silicones, can be found in Encyclopedia of Polymer Science and Engineering, Volume 15, Second Edition, pp 204–308, John Wiley & Sons, Inc., 1989, which is incorporated herein by reference in its entirety.

Silicone materials and silicone resins in particular, can conveniently be identified according to a shorthand nomenclature system well known to those skilled in the art as the "MDTQ" nomenclature. Under this system, the silicone is described according to the presence of various siloxane monomer units which make up the silicone. Briefly, the symbol M denotes the monofunctional unit $(CH_3)_3SiO_{0.5}$; D denotes the difunctional unit $(CH_3)_2SiO$; T denotes the trifunctional unit $(CH_3)SiO_{1.5}$; and Q denotes the quadri- or tetra-functional unit $SiO_2$. Primes of the unit symbols, e.g., M', D', T', and Q' denote substituents other than methyl, and must be specifically defined for each occurrence. Typical alternate substituents include groups such as vinyl, phenyl, amino, hydroxyl, etc. The molar ratios of the various units, either in terms of subscripts to the symbols indicating the total number of each type of unit in the silicone, or an average thereof, or as specifically indicated ratios in combination with molecular weight, complete the description of the silicone material under the MDTQ system. Higher relative molar amounts of T, Q, T' and/or Q' to D, D', M and/or or M' in a silicone resin is indicative of higher levels of crosslinking. As discussed before, however, the overall level of crosslinking can also be indicated by the oxygen to silicon ratio.

The silicone resins for use herein which are preferred are MQ, MT, MTQ, MQ and MDTQ resins. Thus, the preferred silicone substituent is methyl. Especially preferred are MQ resins wherein the M:Q ratio is from about 0.5:1.0 to about 1.5:1.0 and the average molecular weight of the resin is from about 1000 to about 10,000.

Hydrocarbon Conditioning Agents

Hydrocarbons are useful herein as conditioning agents. Useful hydrocarbons include straight chain, cyclic, and branched chain hydrocarbons which can be either saturated or unsaturated. The hydrocarbons preferably will have from about 12 to about 40 carbon atoms, more preferably from about 12 to about 30 carbon atoms, and most preferably from about 12 to about 22 carbon atoms. Also encompassed herein are polymeric hydrocarbons of alkenyl monomers, such as polymers of $C_2$–$C_6$ alkenyl monomers. These polymers can be straight or branched chain polymers. The straight chain polymers will typically be relatively short in length, having a total number of carbon atoms as described above in this paragraph. The branched chain polymers can have substantially higher chain lengths. The number average molecular weight of such materials can vary widely, but will typically be up to about 500, preferably from about 200 to about 400, and more preferably from about 300 to about 350. Also useful herein are the various grades of mineral oils. Mineral oils are liquid mixtures of hydrocarbons that are obtained from petroleum. Specific examples of suitable hydrocarbon materials include paraffin oil, mineral oil, dodecane, isododecane, hexadecane, isohexadecane, eicosene, isoeicosene, tridecane, tetradecane, polybutene, polyisobutene, and mixtures thereof. Isododecane, isohexadeance, and isoeicosene are commercially available as Permethyl 99A, Permethyl 101A, and Permethyl 1082, from Presperse, South Plainfield, N.J. A copolymer of isobutene and normal butene is commercially available as Indopol H-100 from Amoco Chemicals. Preferred for use herein are hydrocarbon conditioning agents selected from the group consisting of mineral oil, isododecane, isohexadecane, polybutene, polyisobutene, and mixtures thereof.

Water Soluble Cationic Polymeric Conditioning Agent

Water soluble cationic polymeric conditioning agents are also useful herein. By "water soluble" is meant a polymer which is sufficiently soluble in water to form a substantially clear solution to the naked eye at a concentration of 0.1% in water, i.e. distilled or equivalent, at 25° C. Preferably, the polymer will be sufficiently soluble to form a substantially clear solution at a 0.5% concentration, more preferably at a 1.0% concentration.

The cationic polymers hereof will generally have a weight average molecular weight which is at least about 5,000, typically at least about 10,000, and is less than about 10 million. Preferably, the molecular weight is from about 100,000 to about 2 million. The cationic polymers will generally have cationic nitrogencontaining moieties such as quaternary ammonium or cationic amino moieties, and mixtures thereof.

The cationic charge density is preferably at least about 0.1 meq/gram, more preferably at least about 0.2 meq/gram, and preferably less than about 3.0 meq/gram, more preferably less than about 2.75 meq/gram.

The cationic charge density of the cationic polymer can be determined according to the Kjeldahl Method, which is well-known to those skilled in the art. Those skilled in the art will recognize that the charge density of amino-containing polymers can vary depending upon pH and the isoelectric point of the amino groups. The charge density should be within the above limits at the pH of intended use.

Any anionic counterions can be utilized for the cationic polymers so long as the water solubility criteria is met. Suitable counterions include halides (e.g., Cl, Br, I, or F, preferably Cl, Br, or I), sulfate, and methylsulfate. Others can also be used, as this list is not exclusive.

The cationic nitrogen-containing moiety will be present generally as a substituent, on a fraction of the total monomer units of the cationic hair conditioning polymers. Thus, the cationic polymer can comprise copolymers, terpolymers, etc. of quaternary ammonium or cationic amine-substituted monomer units and other non-cationic units referred to herein as spacer monomer units. Such polymers are known in the art, and a variety can be found in *International Cosmetic Ingredient Dicitonary*, Fifth Edition, 1993, which is incorporated by reference herein in its entirety.

Suitable cationic polymers include, for example, copolymers of vinyl monomers having cationic amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone, and vinyl pyrrolidone. The alkyl and dialkyl substituted monomers preferably have $C_1$–$C_7$ alkyl groups, more preferably $C_1$–$C_3$ alkyl groups. Other suitable spacer monomers include vinyl esters, vinyl alcohol (made by hydrolysis of polyvinyl acetate), maleic anhydride, propylene glycol, and ethylene glycol.

The cationic amines can be primary, secondary, or tertiary amines, depending upon the particular species and the pH of the composition. In general, secondary and tertiary amines, especially tertiary amines, are preferred.

Amine-substituted vinyl monomers can be polymerized in the amine form, and then optionally can be converted to ammonium by a quaternization reaction. Amines can also be similarly quaternized subsequent to formation of the polymer. For example, tertiary amine functionalities can be quaternized by reaction with a salt of the formula R'X wherein R' is a short chain alkyl, preferably a $C_1$–$C_7$ alkyl, more preferably a $C_1$–$C_3$ alkyl, and X is an anion which forms a water soluble salt with the quaternized ammonium.

Suitable cationic amino and quaternary ammonium monomers include, for example, vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salts, trialkyl acryloxyalkyl ammonium salts, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts. The alkyl portions of these monomers are preferably lower alkyls such as the $C_1$–$C_3$ alkyls, more preferably $C_1$ and $C_2$ alkyls. Suitable amine-substituted vinyl monomers for use herein include dialkylaminoalkyl acrylate, dialkylaminoalkyl methacrylate, dialkylaminoalkyl acrylamide, and dialkylaminoalkyl methacrylamide, wherein the alkyl groups are preferably $C_1$–$C_7$ alkyl and more preferably $C_1$–$C_3$, alkyl.

The cationic polymers hereof can comprise mixtures of monomer units derived from amine- and/or quaternary ammonium-substituted monomer and/or compatible spacer monomers.

Suitable water soluble cationic hair conditioning polymers include, for example: copolymers of 1-vinyl-2-pyrrolidone and 1-vinyl-3-methylimidazolium salt (e.g., chloride salt), referred to in the industry by the CTFA designation as polyquaternium-16, which is commercially available from BASF Corporation under the LUVIQUAT tradename (e.g., LUVIQUAT FC 370); copolymers of 1-vinyl-2-pyrrolidone and dimethylaminoethyl methacrylate, referred to as polyquaternium-11, which is commercially available from Gaf Corporation (Wayne, N.J., USA) under the GAFQUAT tradename (e.g., GAFQUAT 755N); cationic diallyl quaternary ammonium-containing polymers, including, for example, dimethyldiallylammonium chloride homopolymer and copolymers of acrylamide and dimethyldiallylammonium chloride, referred to in the industry by the CTFA designations polyquaternium-6 and polyquaternium-7, respectively; and mineral acid salts of amino-alkyl esters of homo- and co-polymers of unsaturated carboxylic acids having from 3 to 5 carbon atoms, as described in U.S. Pat. No. 4,009,256, incorporated herein by reference.

Other cationic polymers that can be used include polysaccharide polymers, such as cationic cellulose derivatives and cationic starch derivatives. Cationic polysaccharide polymer materials suitable for use herein include those of the formula:

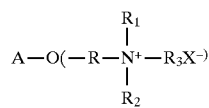

wherein: A is an anhydroglucose residual group, such as a starch or cellulose anhydroglucose residual, R is an alkylene oxyalkylene, polyoxyalkylene, or hydroxyalkylene group, or combination thereof, $R_1$, $R_2$, and $R_3$ independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in $R_1$, $R_2$ and $R_3$) preferably being about 20 or less, and X is an anionic counterion, e.g., halide, sulfate, nitrate, and the like.

Cationic cellulose is available from Amerchol Corp. (Edison, N.J., USA) in their Polymer JR®, LR® and SR® series of polymers, as salts of hydroxyethyl cellulose reacted with trimethyl ammonium substituted epoxide, referred to by the CTFA designation polyquaternium-10. Another type of cationic cellulose includes the polymeric quaternary ammonium salts of hydroxyethyl cellulose reacted with lauryl dimethyl ammonium-substituted epoxide, referred to by the CTFA as polyquatermium-24, and which is available from Amerchol Corp. (Edison, N.J., USA) under the tradename Polymer LM-200®.

Other cationic polymers that can be used include cationic guar gum derivatives, such as guar hydroxypropyltrimonium chloride (conmmercially available from Celanese Corp. in their Jaguar R series). Other materials include quaternary nitrogen-containing cellulose ethers (e.g., as described in U.S. Pat. No. 3,962,418, which is incorporated by reference herein in its entirety), and copolymers of etherified cellulose and starch (e.g., as described in U.S. Pat. No. 3,958,581, which is incorporated herein by reference in its entirety).

Preferred for use herein are water soluble cationic conditioning agents selected from the group consisting of polyquaternium-7, polyquaternium-10, polyquatemnium-11, and mixtures thereof.

Cationic Surfactants

Hair conditioning agents selected from cationic surfactants are useful herein. These surfactants typically contain quaternary nitrogen moieties. The cationic surfactant will preferably, though not necessarily, be insoluble in the compositions hereof. Cationic surfactants among those useful herein are disclosed in the following documents, all of which are incorporated by reference herein in their entirety: M.C. Publishing Co., McCutcheon's, Detergents & Emulsifiers, (North American edition 1979); Schwartz, et al., Surface Active Agents, Their Chemistry and Technology, New York: Interscience Publishers, 1949; U.S. Pat. No. 3,155,591, Hilfer, issued Nov. 3, 1964; U.S. Pat. No. 3,929,678, Laughlin et al., issued Dec. 30, 1975; U.S. Pat. No. 3,959,461, Bailey et al., issued May 25, 1976; and U.S. Pat. No. 4,387,090, Bolich, Jr., issued Jun. 7, 1983.

Among the cationic surfactant materials useful herein are those corresponding to the general formula:

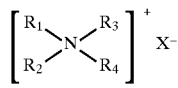

wherein $R_1$, $R_2$, $R_3$, and $R_4$ are independently selected from an aliphatic group of from 1 to about 22 carbon atoms or an aromatic, alkoxy, polyoxyalkylene, alkylamido, hydroxyalkyl, aryl or alkylaryl group having up to about 22 carbon atoms; and X is a salt-forming anion such as those selected from halogen, (e.g. chloride, bromide), acetate, citrate, lactate, glycolate, phosphate nitrate, sulfate, and alkylsulfate radicals. The aliphatic groups can contain, in addition to carbon and hydrogen atoms, ether linkages, and other groups such as amino groups. The longer chain aliphatic groups, e.g., those of about 12 carbons, or higher, can be saturated or unsaturated. Preferred is when $R_1$, $R_2$, $R_3$, and $R_4$ are independently selected from C1 to about $C_{22}$ alkyl. Especially preferred are cationic materials containing two long alkyl chains and two short alkyl chains or those containing one long alkyl chain and three short alkyl chains.

The long alkyl chains in the compounds described in the previous sentence have from about 12 to about 22 carbon atoms, preferably from about 16 to about 22 carbon atoms, and the short alkyl chains in the compounds described in the previous sentence have from 1 to about 3 carbon atoms, preferably from 1 to about 2 carbon atoms.

Also preferred are cationic materials in which at least one of the substituents is selected from hydroxyalkyl, preferably hydroxyethyl or hydroxy propyl, or polyoxyalkylene, preferably polyoxyethylene or polyoxypropylene wherein the total degree of ethoxylation or propoxylation in the molecule from about 5 to about 20. Nonlimiting examples of commercially available materials include Variquat K1215 and 638 from Witco Chemical, Dehyquat SP from Henkel, and Atlas G265 from ICI Americas.

Other cationic materials include the materials having the following CTFA designations: quaternium-8, quaternium-24, quaternium-26, quaternium-27, quaternium-30, quaternium-33, quaternium-43, quaternium-52, quaternium-53, quaternium-56, quaternium-60, quaternium-62, quaternium-70, quaternium-72, quaternium-75, quaternium-77, quaternium-78, quaternium-79, quaternium-80, quaternium-81, quaternium-82, quaternium-83, quaternium-84, and mixtures thereof.

Salts of primary, secondary and tertiary fatty amines are also suitable cationic surfactant materials. The alkyl groups of such amines preferably have from about 12 to about 22 carbon atoms, and can be substituted or unsubstituted. Such amines, useful herein, include stearamido propyl dimethyl amine, diethyl amino ethyl stearamide, dimethyl stearamine, dimethyl soyamine, soyamine, myristyl amine, tridecyl amine, ethyl stearylamine, N-tallowpropane diamine, ethoxylated (with 5 moles of ethylene oxide) stearylamine, dihydroxy ethyl stearylamine, and arachidylbehenylamine. Suitable amine salts include the halogen, acetate, phosphate, nitrate, citrate, lactate, and alkyl sulfate salts. Such salts include stearylamine hydrochloride, soyamine chloride, stearylamine format, N-tallowpropane diamine dichloride and stearamidopropyl dimethylamine citrate. Cationic amine surfactants included among those useful in the present invention are disclosed in U.S. Pat. No. 4,275,055, Nachtigal, et al., issued Jun. 23, 1981, which is incorporated by reference herein in its entirety.

Preferred cationic surfactants are those selected from the group consisting of ditallow dimethyl ammonium chloride, monotallow trimethyl ammonium chloride, dicetyl dimethyl ammonium chloride, cetyl trimethyl ammonium chloride, stearyl trimethyl ammonium chloride, beheneyl trimethyl ammonium chloride, and mixtures thereof.

Water

The compositions of the present invention comprise water. The exact level of water will vary with the levels of the remaining components present. Generally, the compositions of the present invention comprise from about 20% to about 94.05%, preferably from about 50% to about 92%, and more preferably from about 60% to about 90% water. In alternative embodiments, the level of water is can be as high as 94.94%.

Additional Components

In addition to the required components, the compositions herein can also contain a wide variety of additional components. Nonlimiting examples of these additional components are disclosed in International Cosmetic Ingredient Dictionary, Fifth Edition, 1993, and CTFA Cosmetic Ingredient Handbook, Second Edition, 1992, both of which are incorporated by reference herein in their entirety. Some nonlimiting examples of such components are disclosed below.

Polyalkylene Glycols

Although not required, a highly preferred optional component of the present invention is a polyalkylene glycol. When present, the polyalkylene glycol is typically used at a level from about 0.025% to about 1.5%, preferably from about 0.05% to about 1%, and more preferably from about 0.1% to about 0.5% of the compositions of the present invention.

The polyalkylene glycols are characterized by the general formula:

wherein R is selected from the group consisting of H, methyl, and mixtures thereof. When R is H, these materials are polymers of ethylene oxide, which are also known as polyethylene oxides, polyoxyethylenes, and polyethylene glycols. When R is methyl, these materials are polymers of propylene oxide, which are also known as polypropylene oxides, polyoxypropylenes, and polypropylene glycols. When R is methyl, it is also understood that various positional isomers of the resulting polymers can exist.

In the above structure, n has an average value of from about 1500 to about 25,000, preferably from about 2500 to about 20,000, and more preferably from about 3500 to about 15,000.

Polyethylene glycol polymers useful herein are PEG-2M wherein R equals H and n has an average value of about 2,000 (PEG-2M is also known as Polyox WSR® N-10, which is available from Union Carbide and as PEG-2,000); PEG-5M wherein R equals H and n has an average value of about 5,000 (PEG-5M is also known as Polyox WSR® N-35 and Polyox WSR® N-80, both available from Union Carbide and as PEG-5,000 and Polyethylene Glycol 300,000); PEG-7M wherein R equals H and n has an average value of about 7,000 (PEG-7M is also known as Polyox WSR® N-750 available from Union Carbide); PEG-9M wherein R equals H and n has an average value of about 9,000 (PEG 9-M is also known as Polyox WSR® N-3333 available from Union Carbide); and PEG-14 M wherein R equals H and n has an average value of about 14,000 (PEG-14M is also known as Polyox WSR® N-3000 available from Union Carbide).

Other useftu polymers include the polypropylene glycols and mixed polyethylene/polypropylene glycols.

Suspending Agents

Another highly preferred optional component is a suspending agent, which is useful for suspending the silicone hair conditioning agent, when present, in dispersed form in the shampoo compositions. The suspending agent will generally comprise from about 0.1% to about 10%, and more typically from about 0.3% to about 5.0%, by weight, of the shampoo composition. Preferred suspending agents include acyl derivatives, long chain amine oxides, and mixtures thereof. When used in the shampoo compositions, these preferred suspending agents are present in the composition in crystalline form. These suspending agents are described in U.S. Pat. No. 4,741,855, which is incorporated herein by reference in its entirety. These preferred suspending agents include ethylene glycol esters of fatty acids preferably having from about 16 to about 22 carbon atoms. More preferred are the ethylene glycol stearates, both mono and distearate, but particularly the distearate containing less than about 7% of the mono stearate. Other suitable suspending agents include alkanol amides of fatty acids, preferably having from about 16 to about 22 carbon atoms, more preferably about 16 to 18 carbon atoms, preferred examples of which inclucde stearic monoethanolamide, stearic diethanolamide, stearic monoisopropanolamide and stearic monoethanolamide stearate. Other long chain acyl derivatives include long chain esters of long chain fatty acids (e.g., stearyl stearate, cetyl palmitate, etc.); glyceryl esters (e.g., glyceryl distearate) and long chain esters of long chain alkanol amides (e.g., stearamide diethanolamide distearate, stearamide monoethanolamide stearate). Long chain acyl derivatives, ethylene glycol esters of long chain carboxylic acids, long chain amine oxides, and alkanol amides of long chain carboxylic acids in addition to the preferred materials listed above may be used as suspending agents. For example, it is contemplated that suspending agents with long chain hydrocarbyls having $C_8$–$C_{22}$ chains may be used.

Other long chain acyl derivatives suitable for use as suspending agents include N,N-dihydrocarbyl amido benzoic acid and soluble salts thereof (e.g., Na and K salts), particularly N,N-di(hydrogenated) $C_{16}$, $C_{18}$ and tallow amido benzoic acid species of this family, which are commercially available from Stepan Company (Northfield, Ill., USA).

Examples of suitable long chain amine oxides for use as suspending agents include alkyl ($C_{16}$–$C_{22}$) dimethyl amine oxides, e.g., stearyl dimethyl amine oxide.

Other suitable suspending agents include xanthan gum. The use of xanthan gum as a suspending agent in silicone containing shampoo compositions is described, for example, in U.S. Pat. No. 4,788,006, which is incorporated herein by reference in its entirety. Combinations of long chain acyl derivatives and xanthan gum may also be used as a suspending agent in the shampoo compositions. Such combinations are described in U.S. Pat. No. 4,704,272, which is incorporated herein by reference in its entirety.

Other suitable suspending agents include carboxyvinyl polymers. Preferred among these polymers are the copolymers of acrylic acid crosslinked with polyallylsucrose as described in U.S. Pat. No. 2,798,053, which is incorporated herein by reference in its entirety. Examples of these polymers include the carbomers, which are hompolymers of acrylic acid crosslinked with an allyl ether of pentaerythrotol, an allyl ether of sucrose, or an allyl ether of propylene. Preferred carboxyvinyl polymers have a molecular weight of at least about 750,000; more preferred are carboxyvinyl polymers having a molecular weight of at least about 1,250,000; most preferred are carboxyvinyl polymers having a molecular weight of at least about 3,000,000.

Other suitable suspending agents can be used in the shampoo compositions, including those that can impart a gel-like viscosity to the composition, such as water soluble or colloidally water soluble polymers like cellulose ethers such as hydroxyethyl cellulose, and materials such as guar gum, polyvinyl alcohol, polyvinyl pyrrolidone, hydroxypropyl guar gum, starch and starch derivatives, and other thickeners, viscosity modifiers, gelling agents, etc. Mixtures of these materials can also be used.

Other Materials

Other materials useful in the compositions of the present invention include, but are not limited to, preservatives such as benzyl alcohol, benzoic acid, methyl paraben, propyl paraben, imidazolidinyl urea, iodopropynyl butyl carbamate, methylisothiazolinone, methylchloroisothiazolinone; salts and electrolytes such as sodium chloride, potassium chloride, and sodium sulfate; ammonium xylene sulfonate; propylene glycol; polyvinyl alcohol; ethyl alcohol; pH adjusting agents such as citric acid, succinic acid, phosphoric acid, sodium hydroxide, and sodium carbonate; fragrances and colorings to modify the aesthetic appeal of the composition; hydrogen peroxide; sunscreening agents; hair coloring agents; humectants such as glycerol and other polyhydric alcohols; moisturizers; humectants; antioxidants; and chelating agents such as EDTA; antiinflammatory agents; steroids; topical anesthetics; and scalp sensates such as menthol.

Antidandruff agents can also be used in the shampoo compositions of the present invention. These agents include particulate antidandruff agents such as pyridinethione salts, selenium compounds such as selenium disulfide, and soluble antidandruff agents. The concentration of such antidandruff agents will generally range from about 0.1% to about 4% and preferably about 0.2% to about 2%, by weight of the shampoo compositions.

Pediculicides can also be used in the shampoo compositions for control of lice infestations. Suitable pediculicides are well known in the art and include, for example, pyrethrins such as those described in U.S. Pat. No. 4,668,666, which description is incorporated herein by reference in its entirety.

As with all compositions, the present invention should not contain components which unduly interfere with the performance of the compositions.

METHOD OF USE

The conditioning shampoos of the present invention are used in a conventional manner for cleansing and conditioning the hair on human heads. An effective amount of the shampoo composition, typically from about 1 gram to about 50 grams, and preferably from about 1 gram to about 20 grams, is applied to the hair. Preferably the hair has been wetted with water before application of the shampoo. Application of the shampoo typically includes working the composition through the hair, generally with the hands and fingers, to generate a lather. The shampoo product is then typically rinsed from the hair with water. This method for cleansing and conditioning the hair comprises the steps of:

(a) wetting the hair with water, (b) applying an effective amount of the conditioning shampoo of the present invention to the hair, (c) shampoo the hair with the composition, i.e. working the composition in contact with the hair and into a lather, and (d) rinsing the conditioning shampoo from the hair using water.

These steps can be repeated as many times as desired to achieve the cleansing and conditioning benefit sought.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Ingredients are identified by chemical or CTFA name.
Method of Preparation Examples I–X The conditioning shampoo compositions of the present invention can be prepared by using conventional mixing and formulating techniques. The conditioning shampoo compositions illustrated in Examples I–X are prepared in the following manner. All percentages are based on weight unless otherwise specified.

First, a silicone premix is prepared having the following composition by weight: at least about 50% dimethicone, from about 5% to about 15% ammonium laureth-3 sulfate, and the remainder water. It should be noted that the ammonium laureth-3 sulfate is added in this premix, in the main body of the composition, and after heat processing. The premix is formed by high sheer mixing until the desired silicone particle size is achieved.

For each of the compositions illustrated in Examples I–X, polyquaternium-10 and the polyethylene glycol, when present, are dispersed in water to give a solution. This solution, the mineral oil, and approximately one-third of the total ammonium laureth-3 sulfate are combined in a mixing tank and heated to about 75° C. with slow agitation to form a solution of the surfactant. The cocamide MEA, any fatty alcohols, fatty acids, and their derivatives, as applicable, are added to this tank and dispersed with stirring. Next, the ethylene glycol distearate is added to the vessel with mixing. After the addition and mixing of the ethylene glycol distearate is completed, usually after about 5 to 20 minutes, any additional cationic surfactants and the preservatives are added with mixing. The resultant mixture is passed through a heat exchanger, cooled to about 35° C., and collected in a finishing tank. Next, the remainder of the ammonium laureth-3 sulfate, the ammonium lauryl sulfate, any additional surfactants, the silicone premix, and any other remaining ingredients are added with mixing to form a homogeneous mixture. As necessary, the viscosity of the resultant composition can be adjusted by the addition of appropriate amounts of ammonium xylene sulfonate or additional sodium chloride. Preferred viscosities range from about 2000 to about 9000 centistokes at 25° C., as measured by a Wells-Brookfield viscometer equipped with a cone number CP 41 at a measuring speed of 1 rpm.

The compositions illustrated in Examples I–X, all of which are embodiments of the present invention, are useful for both cleansing and conditioning the hair from a single product. In alternative embodiments, the ammonium laureth-3 sulfate and/or the ammonium lauryl sulfate are replaced with equal weights of sodium laureth-3 sulfate and sodium lauryl sulfate, respectively.

| Ingredient | Example Number | | | | |
|---|---|---|---|---|---|
| | I | II | III | IV | V |
| | Percent By Weight | | | | |
| Ammonium Laureth-3 Sulfate | 15.0 | 12.0 | 12.0 | 12.0 | 12.0 |
| Ammonium Lauryl Sulfate | 5.0 | 4.0 | 4.0 | 4.0 | 4.0 |
| Polyquaternium-10 | 0.5 | 1.0 | 1.0 | 1.0 | 1.0 |
| Mineral Oil | 0.5 | 1.0 | 1.0 | 1.0 | 1.0 |
| Dimethicone | 2.0 | 2.5 | 2.0 | 2.0 | 2.0 |
| Cetyl Alcohol | 0.7 | 0.7 | 0.7 | 0.7 | 0.7 |
| Stearyl Alcohol | 0.3 | 0.3 | 0.3 | 0.3 | 0.3 |
| Behenyl Trimethylammonium Chloride | 0 | 0 | 0 | 0.5 | 0.5 |
| Cocamidopropylbetaine | 0 | 0 | 0 | 0.5 | 0 |
| Sodium Lauroyl Sarcosinate | 0 | 0 | 0 | 0 | 2.0 |
| Polyethylene Glycol | 0 | 0 | 0.5 | 0.5 | 0.5 |
| Cocamide MEA | 0.9 | 0.9 | 0.7 | 0.7 | 0.7 |
| Ethylene Glycol Distearate | 2.0 | 2.0 | 1.6 | 1.6 | 1.6 |
| Fragrance | 0.5 | 0.5 | 0.5 | 0.5 | 0.5 |
| DMDM Hydantoin | 0.20 | 0.20 | 0.20 | 0.20 | 0.20 |
| Water | q.s. to 100% | | | | |

| Component | Example Number | | | | |
|---|---|---|---|---|---|
| | VI | VII | VIII | IX | X |
| | Percent By Weight | | | | |
| Ammonium Laureth-3 Sulfate | 12.0 | 12.0 | 12.0 | 12.0 | 12.0 |
| Ammonium Lauryl Sulfate | 4.0 | 4.0 | 4.0 | 4.0 | 4.0 |
| Polyquaternium-10 | 1.0 | 1.0 | 1.0 | 1.0 | 1.0 |

| | | | | | |
|---|---|---|---|---|---|
| Mineral Oil | 1.0 | 1.0 | 1.0 | 1.0 | 1.0 |
| Dimethicone | 2.0 | 2.5 | 2.0 | 2.0 | 2.0 |
| Cetyl Alcohol | 1.0 | 1.4 | 0.42 | 0.7 | 0.63 |
| Stearyl Alcohol | 0.5 | 0.6 | 0.18 | 0.3 | 0.27 |
| iso-Stearyl Alcohol | 0 | 0 | 0 | 0 | 0.1 |
| Palmitic Acid | 0 | 0 | 0 | 0.5 | 0 |
| Steareth-2 | 0 | 0 | 0.9 | 0 | 0 |
| Sodium Lauroyl Sarcosinate | 2.0 | 0 | 0 | 0 | 0 |
| Polyethylene glycol | 0.5 | 0.5 | 6.5 | 0.5 | 0.5 |
| Cocamide MEA | 0.7 | 0.7 | 0.7 | 0.7 | 0.7 |
| Ethylene Glycol Distearate | 1.6 | 1.6 | 1.6 | 1.6 | 1.6 |
| Fragrance | 0.5 | 0.5 | 0.5 | 0.5 | 0.5 |
| DMDM Hydantoin | 0.20 | 0.20 | 0.20 | 0.20 | 0.20 |
| Water | q.s. to 100% | | | | |

Method of Preparation Examples XI–XIII

The conditioning shampoo compositions illustrated in Examples XI–XIII are prepared in the following manner. All percentages are based on weight unless otherwise specified.

For each of the compositions illustrated in Examples XI–XIII, polyquaternium-10 and the polyethylene glycol, when present, are dispersed in water to give a solution. This solution, the mineral oil, and approximately one-third of the total ammonium laureth-3 sulfate are combined in a mixing tank and heated to about 75° C. with slow agitation to form a solution of the surfactant. The cocamide MEA, any fatty alcohols, fatty acids, and their derivatives, as applicable, are added to this tank and dispersed with stirring. Next, the ethylene glycol distearate is added to the vessel with mixing. After the addition and mixing of the ethylene glycol distearate is completed, usually after about 5 to 20 minutes, any additional cationic surfactants and the preservatives are added with mixing. The resultant mixture is passed through a heat exchanger, cooled to about 35° C., and collected in a finishing tank. Next, the remainder of the ammonium laureth-3 sulfate, the ammonium lauryl sulfate, any additional surfactants, the silicone premix, and any other remaining ingredients are added with mixing to form a homogeneous mixture. As necessary, the viscosity of the resultant composition can be adjusted by the addition of appropriate amounts of ammonium xylene sulfonate or additional sodium chloride. Preferred viscosities range from about 2000 to about 9000 centistokes at 25° C., as measured by a Wells-Brookfield viscometer equipped with a cone number CP 41 at a measuring speed of 1 rpm.

The compositions illustrated in Examples XI–XIII, all of which are embodiments of the present invention, are useful for both cleansing and conditioning the hair from a single product. In alternative embodiments, the ammonium laureth-3 sulfate and/or the ammonium lauryl sulfate are replaced with equal weights of sodium laureth-3 sulfate and sodium lauryl sulfate, respectively.

| | Example Number | | |
|---|---|---|---|
| | XI | XII | XIII |
| Ingredient | Percent By Weight | | |
| Ammonium Laureth-3 Sulfate | 12.0 | 12.0 | 12.0 |
| Ammonium Lauryl Sulfate | 4.0 | 4.0 | 4.0 |
| Polyquaternium-10 | 1.0 | 1.0 | 1.0 |
| Mineral Oil | 1.0 | 1.0 | 1.0 |
| Cetyl Alcohol | 0.7 | 1.4 | 1.4 |
| Stearyl Alcohol | 0.3 | 0.6 | 0.6 |
| Sodim Lauroyl Sarcosinate | 2.0 | 0 | 0 |
| Behenyl Trimethylammonium Chloride | 0.5 | 1.0 | 0 |
| Polyethylene Glycol | 0.5 | 0.5 | 0.5 |
| Cocamide MEA | 0.7 | 0.7 | 0.7 |
| Ethylene Glycol Distearate | 1.6 | 1.6 | 1.6 |
| Fragrance | 0.5 | 0.5 | 0.5 |
| DMDM Hydantoin | 0.20 | 0.20 | 0.20 |
| Water | q.s. to 100% | | |

What is claimed is:

1. A hair conditioning shampoo composition comprising:
   (a) from about 5% to about 50%, by weight, of a detersive surfactant selected from the group consisting of anionic surfactants, nonionic surfactants, amphoteric surfactants, zwitterionic surfactants, and mixtures thereof;
   (b) from about 0.9% to about 10%, by weight, of a fatty compound selected from the group consisting of fatty alcohols, fatty acids, alkyl ethers of fatty alcohols, alkoxylated fatty alcohols, alkyl ethers of alkoxylated fatty alcohols, fatty acid esters of fatty alcohols having from about 10 to about 30 carbon atoms, fatty acid esters of alkyl ethers of fatty alcohols, fatty acid esters of alkoxylated fatty alcohols, fatty acid esters of alkyl ethers of alkoxylated fatty alcohols, hydroxy-substituted fatty acids, and mixtures thereof;
   (c) from about 0.05% to about 20%, by weight, of a water soluble cationic polymeric conditioning agent;
   (d) from about 0.025% to about 1.5%, by weight, polyalkylene glycol;
   (e) from about 90% to about 94.05%, by weight, water; and
   (f) a nonvolatile dispersed silicone conditioning agent comprising an arylated silicone having a refractive index of about 1.46 or higher.

2. A composition according to claim 1 wherein said fatty compound is selected from the group consisting of cetyl alcohol, stearyl alcohol, isostearyl alcohol, oleyl alcohol, palmitic acid, stearic acid, steareth-2, steareth-4, ceteth-2, glycerol monostearate, 12-hydroxy stearic acid, and mixtures thereof.

3. A composition according to claim 2 wherein said nonvolatile dispersed silicone conditioning agent is dimethicone; said hydrocarbon conditioning agent is selected from the group consisting of mineral oil, isododecane, isohexadecane, polybutene, polyisobutene, and mixtures thereof; said water soluble cationic polymeric conditioning agent is selected from the group consisting of polyquaternium-7, polyquaternium-10, polyquaternium-11, and mixtures thereof; and said cationic surfactant is selected from the group consisting of ditallow dimethyl ammonium chloride, monotallow trimethyl ammonium chloride, dicetyl dimethyl ammonium chloride, cetyl trimethyl anunonium chloride, stearyl trimethyl ammonium chloride, beheneyl trimethyl ammonium chloride, and mixtures thereof.

4. A composition according to claim 1, wherein the polyalkylene glycol has the formula:

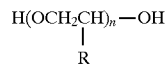

wherein R is selected from the group consisting of H, methyl and mixtures thereof, and n is an integer from about 1500 to about 25,000.

5. A composition according to claim 4 wherein R is H.

6. A hair conditioning shampoo composition comprising:
(a) from about 5% to about 50%, by weight, of a detersive surfactant selected from the group consisting of anionic surfactants, nonionic surfactants, amphoteric surfactants, zwitterionic surfactants, and mixtures thereof;
(b) from about 0.01% to about 10%, by weight, of a fatty compound selected from the group consisting of fatty acids, alkyl ethers of fatty alcohols, alkoxylated fatty alcohols, alkyl ethers of alkoxylated fatty alcohols, fatty acid esters of fatty alcohols having from about 10 to about 30 carbon atoms, fatty acid esters of alkyl ethers of fatty alcohols, fatty acid esters of alkoxylated fatty alcohols, fatty acid esters of alkyl ethers of alkoxylated fatty alcohols, hydroxy-substituted fatty acids, and mixtures thereof;
(c) from about 0% to about 9.99%, by weight, of a fatty alcohol;
(d) from about 0.05% to about 20%, by weight, of a water soluble cationic polymeric conditioning agent;
(e) silicone resin; and
(f) from about 90% to about 94.05%, by weight, water; and
(g) a nonvolatile dispersed silicone conditioning agent comprising an arylated silicone having a refractive index of about 1.46 or higher;
wherein the sum total weight percentage of said fatty compound selected from the group consisting of fatty acids, alkyl ethers of fatty alcohols, alkoxylated fatty alcohols, alkyl ethers of alkoxylated fatty alcohols, fatty acid esters of fat alcohols having from about 10 to about 30 carbon atoms, fatty acid esters of alkyl ethers of fatty alcohols, fatty acid esters of alkoxylated fatty alcohols, fatty acid esters of alkyl ethers of alkoxylated fatty alcohols, hydroxy-substituted fatty acids, and mixtures thereof, and said fatty alcohol is from about 0.01% to about 10%, by weight of the comnposition.

7. A composition according to claim 6 wherein said composition comprises from about 0.6% to about 8% by weight of said fatty compound selected from the group consisting of fatty acids, alkyl ethers of fatty alcohols, alkoxylated fatty alcohols, alkyl ethers of alkoxylated fatty alcohols, fatty acid esters of fatty alcohols having from about 10 to about 30 carbon atoms, fatty acid esters of alkyl ethers of fatty alcohols, fatty acid esters of alkoxylated fatty alcohols, fatty acid esters of alkyl ethers of alkoxylated fatty alcohols, hydroxy-substituted fatty acids, and mixtures thereof; from 0% to about 7.4% by weight of said fatty alcohol; and wherein the sum total weight percentage of said fatty compound selected from the group consisting of fatty acids, alkyl ethers of fatty alcohols, alkoxylated fatty alcohols, alkyl ethers of alkoxylated fatty alcohols, fatty acid esters of fatty alcohols having from about 10 to about 30 carbon atoms, fatty acid esters of alkyl ethers of fatty alcohols, fatty acid esters of alkoxylated fatty alcohols, fatty acid esters of alkyl ethers of alkoxylated fatty alcohols, hydroxy-substituted fatty acids, and mixtures thereof, and said fatty alcohol is from 0.6% to about 8%.

8. A composition according to claim 6 wherein said composition comprises from about 0.9% to about 5% by weight of said fatty compound selected from the group consisting of fatty acids, alkyl ethers of fatty alcohols, alkoxylated fatty alcohols, alkyl ethers of alkoxylated fatty alcohols, fatty acid esters of fatty alcohols having from about 10 to about 30 carbon atoms, fatty acid esters of alkyl ethers of fatty alcohols, fatty acid esters of alkoxylated fatty alcohols, fatty acid esters of alkyl ethers of alkoxylated fatty alcohols, hydroxy-substituted fatty acids, and mixtures thereof; from 0% to about 4.1% by weight of said fatty alcohol; and wherein the sum total weight percentage of said fatty compound selected from the group consisting of fatty acids, alkyl ethers of fatty alcohols, alkoxylated fatty alcohols, alkyl ethers of alkoxylated fatty alcohols, fatty acid esters of fatty alcohols having from about 10 to about 30 carbon atoms, fatty acid esters of alkyl ethers of fatty alcohols, fatty acid esters of alkoxylated fatty alcohols, fatty acid esters of alkyl ethers of alkoxylated fatty alcohols, hydroxy-substituted fatty acids, and mixtures thereof, and said fatty alcohol is from 0% to about 5%.

9. A composition according to claim 6 wherein said composition comprises from about 1% to about 5% by weight of said fatty compound selected from the group consisting of fatty acids, alkyl ethers of fatty alcohols, alkoxylated fatty alcohols, alkyl ethers of alkoxylated fatty alcohols, fatty acid esters of fatty alcohols having from about 10 to about 30 carbon atoms, fatty acid esters of alkyl ethers of fatty alcohols, fatty acid esters of alkoxylated fatty alcohols, fatty acid esters of alkyl ethers of alkoxylated fatty alcohols, hydroxy-substituted fatty acids, and mixtures thereof; from 0% to about 4% by weight of said fatty alcohol; and wherein the sum total weight percentage of said fatty compound selected from the group consisting of fatty acids, alkyl ethers of fatty alcohols, alkoxylated fatty alcohols, alkyl ethers of alkoxylated fatty alcohols, fatty acid esters of fatty alcohols having from about 10 to about 30 carbon atoms, fatty acid esters of alkyl ethers of fatty alcohols, fatty acid esters of alkoxylated fatty alcohols, fatty acid esters of alkyl ethers of alkoxylated fatty alcohols, hydroxy-substituted fatty acids, and mixtures thereof, and said fatty alcohol is from 0% to about 5%.

10. A composition according to claim 6 wherein said fatty compound is selected from the group consisting of cetyl alcohol, stearyl alcohol, isostearyl alcohol, oleyl alcohol, palmitic acid, stearic acid, steareth-2, steareth-4, ceteth-2, glycerol monostearate, 12-hydroxy stearic acid, and mixtures thereof.

11. A hair conditioning shampoo composition according to claim 6 comprising from about 0.05% to about 20%, by weight, of the nonvolatile dispersed silicone conditioning agent.

12. A composition according to claim 11 wherein said nonvolatile dispersed silicone conditioning agent is dimethicone; said hydrocarbon conditioning agent is selected from the group consisting of mineral oil, isododecane, isohexadecane, polybutene, polyisobutene, and mixtures thereof, said water soluble cationic polymeric conditioning agent is selected from the group consisting of polyquaternium-7, polyquaternium-10, polyquaternium-11, and mixtures thereof; and said cationic surfactant is selected from the group consisting of ditallow dimethyl ammonium chloride, monotallow trimethyl ammonium chloride, dicetyl dimethyl ammonium chloride, cetyl trimethyl anunonium chloride, stearyl trimethyl ammonium chloride, beheneyl trimethyl ammonium chloride, and mixtures thereof.

13. A composition according to claim 12 which further comprises from about 0.025% to about 1.5% by weight of a polyalkylene glycol corresponding to the formula:

wherein R is selected from the group consisting of H, methyl, and mixtures thereof, and n is an integer from about 1500 to about 25,000.

14. A composition according to claim 13 wherein R is H.

15. A hair conditioning shampoo composition comprising:
(a) from about 5% to about 50%, by weight, of a detersive surfactant selected from the group consisting of anionic surfactants, nonionic surfactants, amphoteric surfactants, zwitterionic surfactants, and mixtures thereof;
(b) from about 0.9% to about 10%, by weight, of a fatty compound selected from the group consisting of fatty alcohols, fatty acids, alkyl ethers of fatty alcohols, alkoxylated fatty alcohols, alkyl ethers of alkoxylated fatty alcohols, fatty acid esters of fatty alcohols having from about 10 to about 30 carbon atoms, fatty acid esters of alkyl ethers of fatty alcohols, fatty acid esters of alkoxylated fatty alcohols, fatty acid esters of alkyl ethers of alkoxylated fatty alcohols, hydroxy-substituted fatty acids, and mixtures thereof;
(c) from about 0.05% to about 20%, by weight, of a water soluble cationic polymeric conditioning agent;
(d) from about 0.05% to about 20%, by weight, of a hair conditioning agent selected from the group consisting of hydrocarbon conditioning agents, cationic surfactants, and mixtures thereof;
(e) from about 0% to about 19.95%, by weight, of a nonvolatile dispersed silicone conditioning agent comprising an arylated silicone having a refractive index of about 1.46 or higher;
(f) from about 0.025% to about 1.5%, by weight polyalkylene glycol; and
(g) from about 90% to about 94.05%, by weight, water, wherein the sum total concentration of said water soluble cationic polymeric conditioning agent, said hair conditioning agent selected from the group consisting of hydrocarbon coniditioning agents, cationic surfactants, and mixtures thereof and said nonvolatile dispersed silicone conditioning agent is from about 0.05% to about 20% by weigh of the composition.

16. A composition according to claim 15 wherein said composition comprises from about 0.6% to about 10% by weight of said fatty compound selected from the group consisting of fatty alcohols, fatty acids, alkyl ethers of fatty alcohols, alkoxylated fatty alcohols, alkyl ethers of alkoxylated fatty alcohols, fatty acid esters of fatty alcohols having from about 10 to about carbon atoms, fatty acid esters of alkyl ethers of fatty alcohols, fatty acid esters of alkoxylated fatty alcohols, fatty acid esters of alkyl ethers of alkoxylated fatty alcohols, hydroxy-substituted fatty acids, and mixtures thereof.

17. A composition according to claim 15 wherein said composition comprises from about 0.9% to about 10% by weight of said fatty compound selected from the group consisting of fatty alcohols, fatty acids, alkyl ethers of fatty alcohols, alkoxylated fatty alcohols, alkyl ethers of alkoxylated fatty alcohols, fatty acid esters of fatty alcohols having from about 10 to about carbon atoms, fatty acid esters of alkyl ethers of fatty alcohols, fatty acid esters of alkoxylated fatty alcohols, fatty acid esters of alkyl ethers of alkoxylated fatty alcohols, hydroxy-substituted fatty acids, and mixtures thereof.

18. A composition according to claim 15 wherein said composition comprises from about 1% to about 10% by weight of said fatty compound selected from the group consisting of fatty alcohols, fatty acids, alkyl ethers of fatty alcohols, alkoxylated fatty alcohols, alkyl ethers of alkoxylated fatty alcohols, fatty acid esters of fatty alcohols having from about 10 to about 30 carbon atoms, fatty acid esters of alkyl ethers of fatty alcohols, fatty acid esters of alkoxylated fatty alcohols, fatty acid esters of alkyl ethers of alkoxylated fatty alcohols, hydroxy-substituted fatty acids, and mixtures thereof.

19. A composition according to claim 15 wherein said fatty compound is selected from the group consisting of cetyl alcohol, stearyl alcohol, isostearyl alcohol, oleyl alcohol, palmitic acid, stearic acid, steareth-2, steareth-4, ceteth-2, glycerol monostearate, 12-hydroxy stearic acid, and mixtures thereof.

20. A composition according to claim 19 wherein said hydrocarbon conditioning agent is selected from the group consisting of mineral oil, isododecane, isohexadecane, polybutene, polyisobutene and mixtures thereof; said water soluble cationic polymeric conditioning agent is selected from the group consisting of polyquaternium-7, polyquaternium-10, polyquaternium-11 and mixtures thereof; and said cationic surfactant is selected from the group consisting of ditallow dimethyl ammonium chloride, monotallow trimethyl ammonium chloride, dicetyl dimethyl ammonium chloride, cetyl trimethyl ammonium chloride, stearyl trimethyl ammonium chloride, beheneyl trimethyl ammonium chloride and mixtures thereof.

21. A composition according to claim 15 which further comprises from about 0.025% to about 1.5% by weight of a polyalkylene glycol corresponding to the formula:

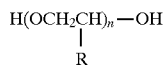

wherein R is selected from the group consisting of H, methyl, and mixtures thereof, and n is an integer from about 1500 to about 25,000.

22. A composition according to claim 21 wherein R is H.

23. A method for cleansing and conditioning the hair comprising the steps of:
(a) wetting the hair with water,
(b) applying an effective amount of the composition of claim 1 to the hair,
(c) shampooing the hair with said composition of claim 1, and
(d) rinsing said composition of claim 1 from the hair using water.

24. A method for cleansing and conditioning the hair comprising the steps of:
(a) wetting the hair with water,
(b) applying an effective amount of the composition of claim 7 to the hair,
(c) shampooing the hair with said composition of claim 7, and
(d) rinsing said composition of claim 7 from the hair using water.

25. A method for cleansing and conditioning the hair comprising the steps of:
(a) wetting the hair with water,
(b) applying an effective amount of the composition of claim 15 to the hair,
(c) shampooing the hair with said composition of claim 15, and (d) rinsing said composition of claim 15 from the hair using water.

26. A hair conditioning shampoo composition according to claim 1 comprising from about 0.05% to about 20%, by weight, of the nonvolatile dispersed silicone conditioning agent.

27. A hair conditioning shampoo composition according to claim 1 further comprising silicone resin.

28. A hair conditioning shampoo composition according to claim 1 wherein the water soluble cationic polymeric conditioning agent has an average molecular weight of at least about 5,000 and a cationic charge density of at least about 0.1 meq/gram.

29. A hair conditioning shampoo composition according to claim 1 wherein the water soluble cationic polymeric conditioning agent is selected from the group consisting of polyquaternium-7, polyquaternium-10, polyquaternium-11, and mixtures thereof.

30. A hair conditioning shampoo composition according to claim 15, further comprising silicone resin.

* * * * *